United States Patent [19]

Press

[11] Patent Number: 4,871,745

[45] Date of Patent: Oct. 3, 1989

[54] 2- OR 3-ARYL SUBSTITUTED IMIDAZO(1,2-A)PYRIDINES AND THEIR USE AS ANTISECRETORY AGENTS

[75] Inventor: Jeffery B. Press, Rocky Hill, N.J.

[73] Assignee: Ortho Pharmaceutical Corporation, Raritan, N.J.

[21] Appl. No.: 258,346

[22] Filed: Oct. 17, 1988

Related U.S. Application Data

[60] Division of Ser. No. 90,111, Aug. 31, 1982, Pat. No. 4,291,117, which is a continuation-in-part of Ser. No. 909,648, Sep. 22, 1996, Pat. No. 4,727,145.

[51] Int. Cl.$^4$ .................... A61K 31/395; A61K 31/40
[52] U.S. Cl. .................................................... 514/300
[58] Field of Search ......................................... 514/300

[56] References Cited

U.S. PATENT DOCUMENTS 4,654,349 3/1987 Irikura et al. ....................... 514/300

Primary Examiner—M. C. Lee
Assistant Examiner—J. Richter
Attorney, Agent, or Firm—Benjamin F. Lambert

[57] ABSTRACT

Novel 2- or 3- aryl substituted imidazo[1,2-a]pyridines and their synthesis are described. The compounds have local anesthetic properties and are useful as local anesthetic agents, calcium channel blocking agents and antisecretory agents.

4 Claims, No Drawings

2- OR 3-ARYL SUBSTITUTED IMIDAZO(1,2-A)PYRIDINES AND THEIR USE AS ANTISECRETORY AGENTS

CROSS-REFERENCE TO RELATED APPLICATION

This is a division of application Ser. No. 90,111, filed Aug. 31, 1987, now U.S. Pat. No. 4,791,117, which is a continuation-in-part of application Ser. No. 909,648, filed Sept. 22, 1986 now U.S. Pat. No. 4,727,145.

BACKGROUND OF THE INVENTION

1. Field of the Invention

The present invention relates to novel 2- or 3-aryl substituted imidazo[1,2-a]pyridines of general formula:

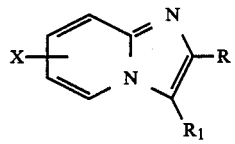

as described further below. The compounds of formula I are useful as local anesthetic agents, calcium channel blocking agents and antisecretory agents. Local anesthetics are known to exhibit antiarrhythmic activity. Calcium channel blocking agents are known to lower blood pressure. The compounds of formula I may further be useful in ophthamlogy.

2. Description of the Prior Art

No examples of local anesthetics with a 2- or 3-aryl substituted imidazo[1,2-a]pyridine structure have been seen in the prior art.

Local anesthetics are drugs which reversibly block nerve conduction near their site of application or injection and thus produce temporary loss of feeling or sensation in a limited area of the body. Local anesthetics are used to prevent pain in surgical procedures, injury, and disease. Local anesthetics can act on any part of the nervous system and on every type of nerve fiber. Since ionic mechanisms of excitability are similar in nerve and muscle, it is not surprising that local anesthetics also have prominent actions on all types of muscular tissue.

Local anesthetics prevent both the generation and the conduction of a nerve impulse. The main site of action is the cell membrane, and there is seemingly little direct action of physiological importance on the axoplasm. The axoplasmic effects that do occur may be secondary to the membrane action.

Known local anesthetics blocks conduction by interfering with the fundamental process in the generation of a nerve action potential, namely, the large transient increase in the permeability of the membrane to sodium ions that is produced by a slight depolarization of the membrane.

One theory of how local anesthetics block nerve conduction is that they compete with calcium at some site that controls the permeability of the membranel Local anesthetics also reduce the permeability of resting nerve to potassium as well as to sodium ions.

Adverse reactions to local anesthetics can be divided into two groups: systemic and local adverse reactions. Systemic adverse reactions are usually associated with high blood levels of the drug and usually result from overdosage, rapid systemic adsorption, or inadvertent intravenous administration. The reactions usually involve the central nervous and cardiovascular systems. Local adverse reactions to known local anesthetic drugs are either cytotoxic or allergic.

SUMMARY OF THE INVENTION

The present invention is directed to 2- or 3-aryl substituted imidazo[1,2-a]pyridines of the formula

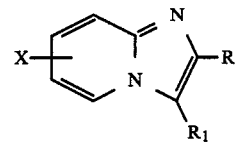

where
X may be hydrogen, halogen, hydroxy, alkoxy having 1-3 carbon atoms, benzyloxy, or $C_1$-$C_6$ alkyl either singularly or in combination;
R may be H or Ar;
$R_1$ may be H, $CH_3$ or Ar;
Ar may be

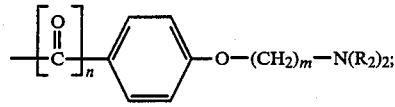

$R_2$ may be a $C_1$-$C_6$ alkyl;
n may be 0 or 1 when R is Ar; or
n may be 1 when $R_1$ is Ar; and
m may be 2-6, with the proviso that both R and $R_2$ cannot be Ar at the same time and at least one of R and $R_1$ is Ar.

The compounds of formula 1 are useful as local anesthetic agents, calcium channel blocking agents and antisecretory agents. Local anesthetics are known to exhibit antiarrhythmic activity. The compounds of formula I may further be useful in ophthamology.

DETAILED DESCRIPTION OF THE INVENTION

The invention in its broadest aspects relates to 2- or 3-aryl substituted imidazo[1,2-a]pyridine compounds which have local anesthetic activity in mammals. The 2- or 3-aryl substituted imidazo[1,2-a]pyridine compounds of the invention demonstrating local anesthetic activity, calcium channel blocking activity and antisecretory activity are shown above.

The preferred compounds of the present invention are those wherein X is hydrogen, bromo, hydroxy, benzyloxy, methyl or dimethyl; $R_2$ is butyl; and m is 3.

The 2-aryl substituted imidazo[1,2-a]pyridine compounds where n is o are prepared in accordance with Scheme I.

Scheme I

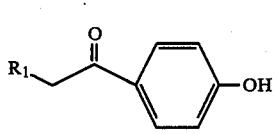

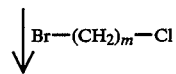

Scheme I
-continued

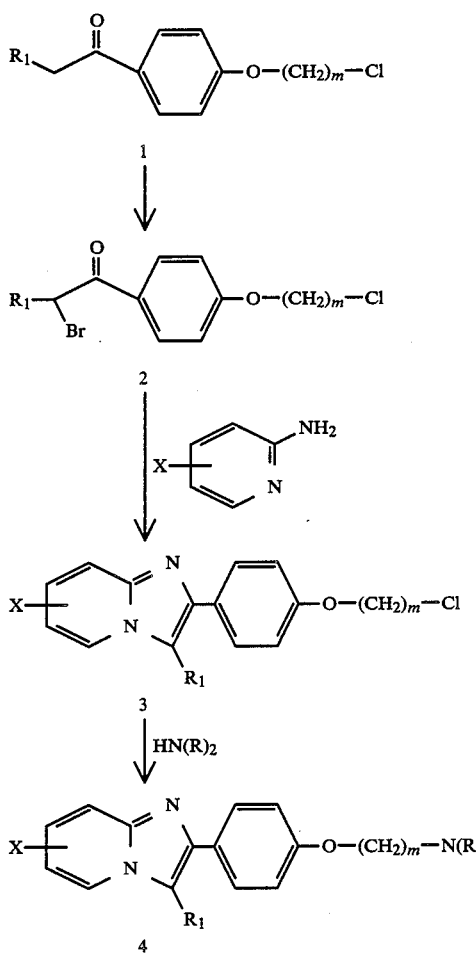

In Scheme I, p-hydroxyacetophenone or p-hydroxypropiophenone, $R_1$ is H or $CH_3$ respectively, is treated with a 1-bromo-ω-chloro alkane such as 1-bromo-2-chloroethane, 1-bromo-3-chloropropane, 1-bromo-4-chlorobutane or 1-bromo-5-chloropentane or 1-bromo-6-chlorohexane by refluxing in an alcoholic base for about 12 to 48 hours to produce a p-chloroalkoxyphenone 1 as a liquid. The alcohol is preferably methanol, and the base may be potassium hydroxide or sodium hydroxide.

The p-chloroalkoxyphenone 1 is then reacted with bromine in either an ether solvent or glacial acetic acid or carbon disulfide. Suitable ethers include tetrahydrofuran, diethyl ether, or dimethoxy ether. The reaction takes place at a temperature of about 10° C. to 65° C. for about 2 to 24 hours to produce α-bromoketone 2.

The α-bromoketone 2 is then subjected to a condensation reaction with 2-aminopyridine or a substituted 2-aminopyridine in an alcoholic solvent. The condensation is conducted at about 65° C. to 86° C. for about 2 to 24 hours to yield a chloroalkoxyphenol imidazopyridine 3. Suitable substituted 2-aminopyridines which may be utilized in the condensation reaction include 3-methyl-2-aminopyridine, 5-bromo-2-aminopyridine, 4-methyl-2-aminopyridine, 3-benzyloxy-2-aminopyridine, 3-hydroxy-2-aminopyridine, and 4,6-dimethyl-2-aminopyridine. The alcoholic solvent may be methanol, ethanol or isopropanol.

The chloroalkoxyphenyl imidazopyridine 3 is treated with an amine solvent, such as dimethylamine, diethylamine, dipropylamine, dibutylamine, dipentylamine or dihexylamine at about 100° C. to 150° C. for 4 to 64 hours to yield the 2-aryl subsituted imidazo[1,2-a]pyridine 4.

The 2-aryl substituted imidazo[1,2-a]pyridines where n is 1 are produced according to Scheme II.

Scheme II

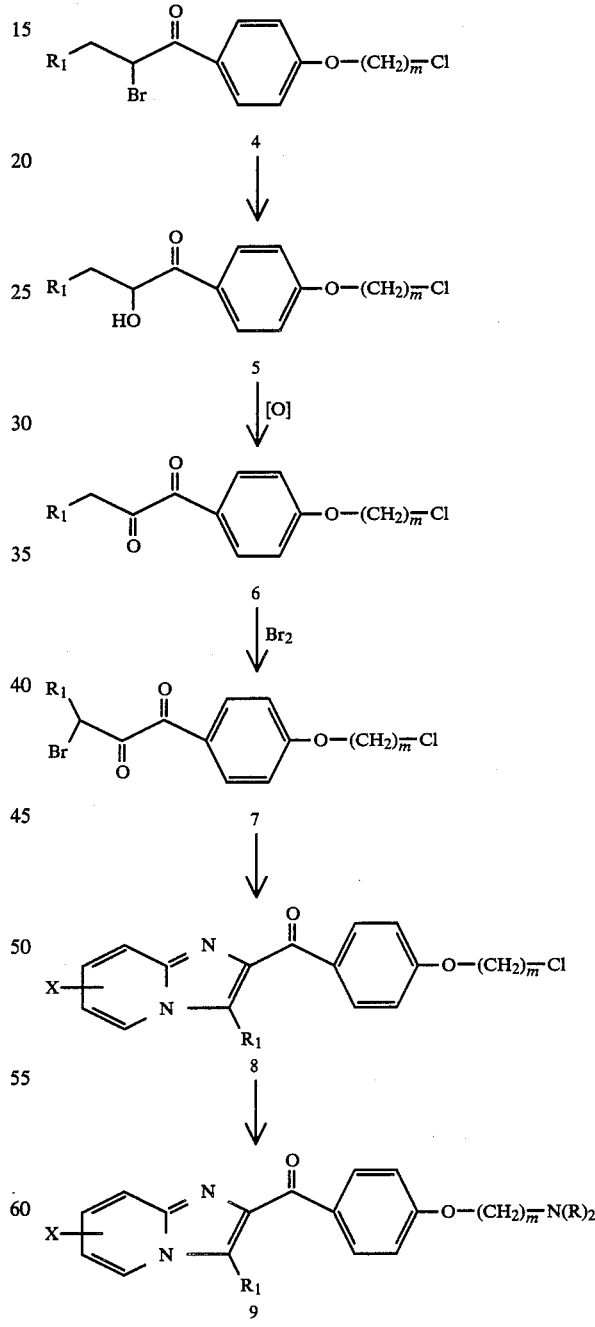

The α-bromoketone 2 which may be prepared as described in Scheme I, is treated in a polar solvent with an aqueous solution of a base, such as sodium hydroxide, at about 20° C. to 50° C. to produce α-hydroxyketone 5. Suitable polar solvents include dimethylformamide, dimethylsulfoxide, hexamethyl phosphoramide and N-methyl pyrrolidone.

The α-hydroxyketone 5 is then oxidized with an oxidizing agent, such as pyridinium chlorochromate, chromium trioxidepyridine, dimethyl sulfoxide-oxalyl chloride or chromic acidsulfuric acid, in an inert solvent to yield a diketone 6. Suitable inert solvents include methylene chloride, chloroform and acetone.

The diketone 6 is reacted with bromine in either an ether solvent glacial acetic acid or carbon disulfide at about 10° C. to 65° C. for about 2 to 24 hours to produce α-bromodiketone 7. Suitable ethers include tetrahydrofuran, diethyl ether or dimethoxyether.

The α-bromodiketone 7 is subjected to the condensation as previously described in Scheme I to produce compound 8 which is reacted with an amine solvent as described in Scheme I to yield the 2-aryl substituted imidazo[1,2-a]pyridines 9.

The 3-aryl substituted imidazo[1,2-a]pyridines where n is 1 are produced in accordance with Scheme III which follows.

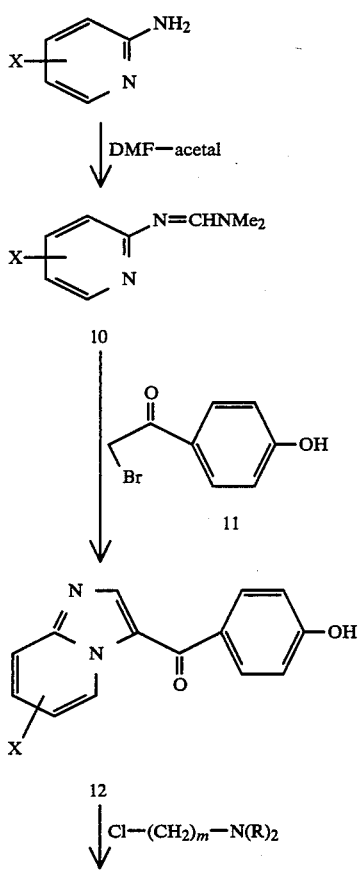

-continued
Scheme III

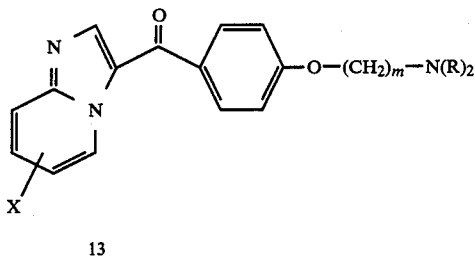

In Scheme III, 2-aminiopyridine or a substituted 2-aminopyridine, such as 3-methyl-2-aminopyridine, 5-bromo-2-aminopyridine, 4-methyl-2-aminopyridine, 3-benzyloxy-2-aminopyridine, 4,6-dimethyl-2-aminopyridine or 3-hydroxy-2-aminopyridine is reacted with dimethylformamide, dimethylacetal or triethyl orthoformate in an inert solvent at about 60° C. to 120° C. for about 4 to 12 hours to produce an amidine 10. Suitable inert solvents include benzene, toluene, xylenes or acetone.

The amidine 10 is then subjected to a condensation reaction with a α-bromoketone 11 in an alcoholic solvent, such as methanol, ethanol or isopropanol at about 60° C. to 85° C. for about 2 to 24 hours toyield a 3-aryl substituted imidazopyridine 12 which is a solid. The α-bromoketone 11 can be produced by reacting p-hydroxyacetophenone with bromine in either an ether solvent or glacial acetic acid or carbon disulfide at a temperature range of about 10° C. to 65° C. for approximately 2 to 24 hours. Suitable ethers include tetrahydrofuran, diethyl ether or dimethoxy ether.

The 3-aryl substituted imidazopyridine 12 is alkylated with a chloroalkyl dialkylamine to yield the 3-aryl substituted imidazo[1,2-a]pyridine 13. The reaction is conducted in an alcoholic base such as potassium hydroxide in methanol and in the presence of catalytic iodine at a temperature of about 60° C. to 80° C. for about 8 to 9 hours. The chloroalkoxy dialkylamine used in the reaction is prepared by treating a 1-bromo-ω-chloroalkane with a dialkylamine at about 100° C. to 150° C.

For topical administration of the compounds of formula I as a local anesthetic, the carrier may take a wide variety of forms depending on the form of preparation, such as creams, dressings, gels, lotions, ointments or liquids. The 2- or 3-aryl substituted imidazo[1,2-a]pyridine will be present in the pharmaceutical composition from about 1% by weight to about 10% by weight, depending on the particular form employed.

An injectable form of the 2- or 3-aryl substituted imidazo[1,2-a]pyridine is usually administered intradermally, subcutaneously, or submucosally across the path of nerves supplying the area to be anethesized. The injection may also be given intramuscularly. The 2- or 3-aryl substituted imidazo-[1,2-a]pyridines will be present in an injectable pharmaceutical composition from about 0.1% by weight to 10% by weight. The injectable preparation may also contain isotonicity adjusting agents such as sodium chloride, pH adjusting agents such as hydrochloric acid and preservatives such as methylparaben. Injectable preparations may be in the form of solutions or suspensions.

The pharmaceutical compositions for local anesthetic use described above, containing a compound of the present invention as the active ingredient in intimate admixture with a pharmaceutical carrier, can be prepared according to conventional pharmaceutical compounding techniques.

Pharmaceutical compositions for calcium channel blocking and antisecretory uses, containing a compound of the present invention as the active ingredient in intimate admixture with a pharmaceutical carrier, can be prepared according to conventional pharmaceutical compounding techniques. The carrier may take a wide variety of forms depending on the form of preparation desired for administration, e.g., intravenous, oral or parenteral. In preparing the compositions in oral dosage form, any of the usual pharmaceutical media may be employed, such as, for example, water, glycols, oils, alcohols, flavoring agents, preservatives, coloring agents and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. For parenterals, the carrier will usually comprise sterile water, through other ingredients, for example, to aid solubility or for preservative purposes, may be included. Injectable suspensions may also be prepared, in which case appropriate liquid carriers, suspending agents and the like may be employed. For these utilities, the pharmaceutical compositions will generally contain per dosage unit, e.g., tablet, capsule, powder, injection, teaspoonful and the like, from about 1.0 to about 100 mg/kg, and preferably from about 5 to about 25 mg/kg of the active ingredient.

The following examples describe the invention in greater particularity and are intended to be a way of illustrating but not limiting the invention.

EXAMPLE I 2-(4-Dibutylaminopropoxyphenyl)imidazo[1,2-a]pyridine

To a mixture of p-hydroxyacetophenone (50.7 g, 0.37 mol) and 1-bromo-3-chloropropane (160 ml, 1.5 mol) in methanol (250 ml) was added portionwise potassium hydroxide (63 g, 1.12 mol). The mixture was stirred at reflux for 24 hours, cooled to room temperature, filtered through Celite and evaporated in vacuo. The residual semi-solid was diluted with diethyl ether (500 ml) and washed with $H_2O$ ($2 \times 300$ ml). The ether solution was dried over $MgSO_4$, filtered and evaporated in vacuo to give p-chloroproxy acetophenone as a liquid in 68% yield (53.38 g). $^1H$ NMR ($CDCl_3$): δ 7.98–7.89 (d, J=8.9 Hz, 2H), 7.02–6.92 (d, J=8.9 Hz, 2H), 4.16 (t, J=5.9 Hz, 2H), 3.75 (t, J=6.4 Hz, 2H), 2.52 (s, 3H), 2.34–2.16 (m, 2H).

To a stirred solution of p-chloropropoxyacetophenone (53.3 g, 0.25 mol) in diethyl ether (250 ml) was slowly added bromine (13 ml, 0.25 mol) and allowed to stir at room temperature for 16 hours. The dark mixture was poured into an aqueous saturated sodium bicarbonate solution (300 ml) and the organic layer separated. The ether layer was washed with an aqueous saturated sodium bicarbonate solution (300 ml) and with water (300 ml) and dried over $MgSO_4$. The solution was filtered and evaporated in vacuo to yield α-bromo-4-chloropropoxy acetophenone (64.4 g, 88% yield) as a dark oil. $^1H$ NMR ($CDCl_3$): δ 7.96 (d, J=8.9 Hz, 2H), 6.95 (d, J=8.9 Hz, 2H), 4.41 (s, 2H), 4.19 (t, 2H), 3.75 (t, 2H), 2.26 (m, 2H).

A mixture of α-bromo-4-chloropropoxy acetophenone (12.8 g, 44 mmol) and 2-aminopyridine (4.0 g, 44 mmol) in ethanol (80 ml) was stirred at reflux for 3 hours, cooled at room temperature and filtered to give 2-(4-chloropropoxyphenyl)imidazo[1,2-a]pyridine (5.2 g, 32% yield) as a white solid. $^1H$ NMR ($CD_3OD$): δ 8.81 (d, J=6.7 Hz, 1H), 8.51 (s, 1H), 7.97–7.01 (m, 7H), 4.19 (t, J=5.9 Hz, 2H), 3.79 (t, J=6.3 Hz, 2H), 2.25 (m, 2H).

A suspension of 2-(4-chloropropoxyphenyl)imidazo[1,2-a]pyridine (5.2 g, 14 mmol) in dibutylamine (30 ml) was stirred at reflux for 5 hours. The excess dibutylamine was removed by distillation and the resulting oil was flash chromatographed (silica gel, 9:1 $CH_2Cl_2$:acetone) to give the free base of the title compound (5.1 g, 93% yield) as an oil. The HCl salt was prepared by dropwise addition of concentrated hydrochloric acid to a solution of the free base in methanol, concentrated and recrystalized from methanol acetone to yield 2-(4-dibutylaminopropoxyphenyl)imidazo[1,2-a]pyridine as a white crystalline solid, mp 179° C. to 183° C. IR(KBr): 3400, 2620, 1650, 1620 cm$^{-1}$. MS: 380 (MH+). $^1H$ NMR ($CD_3OD$): δ 8.80 (d, J=8 Hz, 1H), 8.52 (s, 1H), 7.92–7.49 (m, 5H), 7.18 (d, J=8 Hz, 2H), 4.23 (t, J=4.6 Hz, 2H), 3.50–3.13 (m, 6H), 2.25 (m, 2H), 1.82–1.34 (m, 8H), 1.01 (m, 6H).

Theor. $C_{24}H_{33}N_3O \cdot 3HCl$: C, 58.95; H, 7.42; N, 8.59. Found: C, 59.25; H, 7.71; N, 9.03.

When in the above procedure, 2-amino-6-picoline was used as the starting material, the hydrochloride salt of 2-(4-dibutylaminopropoxyphenyl)-5-methylimidazo[1,2-a]pyridine, mp 221° C. to 223° C., was obtained as the product.

When in the above procedure, p-hydroxypropiophenone is employed as the starting material, 2-(4-dibutylaminopropoxyphenyl)-3-methylimidazo[1,2-a]pyridine is obtained as the resultant product.

EXAMPLE 2

2-(4-Dibutylaminopropoxyphenyl)-8-methylimidazo[1,2-a]pyridine

The title compound was prepared as described above by reacting 3-methyl-2-aminopyridine (6.3 g, 15.8 mmol) with α-bromo-4-chlorophenoxyacetophenone. The product was reacted with dibutylamine as described above to produce (2.0 g, 32% yield) of the free base which was converted to the HCl salt, mp 214° C. to 217° C. IR(KBr): 3420, 2960, 1650, 1615 cm$^{-1}$. MS: 393 (M+). $^1H$ NMR ($CD_3OD$): δ 8.25 (d, J=6 Hz, 1H), 8.06 (s, 1H), 7.88 (d, J=7 Hz, 2H), 7.05 (m, 3H), 6.85 (t, J=6 Hz, 1H), 4.13 (t, J=4 Hz, 2H), 3.00–2.80 (m, 6H), 2.59 (s, 3H), 2.10 (m, 2H), 1.57–1.44 (m, 8H), 1.04 (m, 6H).

Theor. $C_{25}H_{35}N_3O \cdot 3HCl$: C, 59.70; H, 7.62; N, 8.35. Found: C, 59.61; H, 7.69; N, 8.37.

When in the above procedure, 1-bromo-4-chlorobutane was used as the starting material, the hydrochloride salt of 2-(5-dibutylaminiobutoxyphenyl)-8-methylimidazo[1,2-a]pyridine, mp 161° C. to 163° C., was obtained.

When in the above procedure dipropylamine or dimethylamine was employed as the starting material, the corresponding hydrochloride salt of 2-(4-dipropylaminopropoxyphenyl)-8-methylimidazo[1,2- a]pyridine, mp 138° C. to 140° C., or 2-(4-dimethylaminopropoxyphenyl)-8-methylimidazo[1,2-a]pyridine, mp >240° C., was obtained as the resultant product.

EXAMPLE 3

2-(4-Dibutylaminopropoxyphenyl)-6-bromoimidazo[1,2-a]pyridine

5-Bromo-2-aminopyridine (2.0 g, 12 mmol) was reaccted with α-bromo-4-chlorophenoxyacetophenone as described in Example 1. The resulting product was reacted with dibutylamine as described in Example 1 to give the free base of the title compound (2.1 g, 74% yield) which was converted to the HCl salt, mp 193° C. to 195° C. IR(KBr): 3420, 2700, 1650, 1605 cm$^{-1}$. MS: 358 (M+). $^1$H NMR (CD$_3$OD): δ 9.10 (brs, 1H), 8.49 (s, 1H), 8.13–8.01 (dd, J=1.6, 9.6 Hz, 1H), 7.85 (d, J=9.2 Hz, 3H), 7.13 (d, J=8.8 Hz, 2H), 4.22 (t, J=6 Hz, 2H), 3.24 (m, 6H), 2.29 (m, 2H), 1.66–1.40 (m, 8H), 1.02 (m, 6H).

Theor. C$_{24}$H$_{32}$BrN$_3$O.2HCl.H$_2$O: C, 52.47; H, 6.61; N, 7.65. Found: C, 52.06; H, 6.47; N, 7.50.

When in the above procedure, p-hydroxypropiophenone is employed as the starting material, 2-(4-dibutylaminopropoxyphenyl)-3-methyl-6-bromoimidazo[1,2-a]pyridine is obtained as the resultant product.

EXAMPLE 4

2-(4-Dibutylaminopropoxyphenyl)-7-methylimidazo[1,2-a]pyridine

The title compound was produced in accordance with Example 1 by reacting 4-methyl-2-aminopyridine (1.1 g, 10.3 mmol) with α-bromo-4-chlorophenoxy acetophenone and reacting the resulting compound with dibutylamine to yield 1.6 g of the compound (29% yield) as the HCl salt, mp 134° C. to 136° C. IR(KBr): 3440, 2640, 2510 cm$^{-1}$. MS: 393 (M+). $^1$H NMR (CD$_3$OD): δ 8.63 (d, J=6.7 Hz, 1H), 8.37 (s, 1H), 7.84 (d, J=8.8 Hz, 2H), 7.66 (s, 1H), 7.33 (d, J=6.9 Hz, 1H), 7.17 (d, J=8.8 Hz, 2H), 4.22 (t, J=5 Hz, 2H), 3.39–3.13 (m, 6H), 2.60 (s, 3H), 2.28 (m, 2H), 1.76–1.40 (m, 8H), 1.02 (m, 6H).

Theor. C$_{25}$H$_{35}$N$_3$O.3HCl.2H$_2$O: C, 55.71; H, 7.86; N, 7.80. Found: C, 55.57; H, 7.60; N, 7.43.

When in the above procedure, p-hydroxypropiophenone is employed as the starting material, 2-(4-dibutylaminopropoxyphenyl)-3,7-dimethylimidazo[1,2-a]pyridine is obtained as the resultant product.

EXAMPLE 5

2-(4-Dibutylaminopropoxyphenyl)-8-hydroxyimidazo[1,2-a]pyridine

3-Hydroxy-2-aminopyridine (3.8 g, 34.4 mmol) was reacted with α-bromo-4-chlorophenoxyacetophenone as described in Example 1. The resulting product was reacted with dibutylamine as described in Example 1 to produce 5.7 g (69% yield) of the free base of the title compound, which was then converted to the HCl salt, mp 174° C. to 177° C. IR(KBr): 3450, 1640, 1610 cm$^{-1}$. MS: 396 (MH+). $^1$H NMR (CD$_3$OD): δ8.42 (s, 1H), 8.29 (d, J=6 Hz, 1H), 7.87 (d, J=9 Hz, 2H), 7.20 (m, 4H), 4.23 (t, J=6 Hz, 2H), 3.50–3.15 (m, 6H), 2.29 (m, 2H), 1.84–1.29 (m, 8H), 1.02 (m, 6H).

Theor. C$_{24}$H$_{33}$N$_3$O$_2$.3HCl.½H$_2$O: C, 56.09; H, 7.26; N, 8.18. Found: C, 56.00; H, 7.09; N, 7.99.

When in the above procedure, p-hydroxypropiophenone is employed as the starting material, 2-(4-dibutylaminopropoxyphenyl)-3-methyl-8-hydroxyimidazo[1,2-a]pyridine is obtained as the resultant product.

EXAMPLE 6

2-(4-Dibutylaminopropoxyphenyl)-8-benzloxyimidazo[1,2-a]pyridine

The title compound was prepared in accordance with Example 1 by reacting 3-benzyloxy-2-aminopyridine (5.0 g, 25 mmol) with α-bromo-4-chlorophenoxyacetophenone and reacting the resulting product with dibutylamine to yield 6.7 g of the free base (73% yield) which was converted to the HCl salt, mp 153° C. to 156° C. IR(KBr): 3440, 3960, 1620, cm$^{-1}$. MS: 485 (M+). $^1$H NMR (CD$_3$OD): δ 8.46 (s, 1H), 7.87 (d, J=8.8 Hz, 2H), 7.62–7.37 (m, 2H), 7.16 (d, J=8.8 Hz, 2H), 5.49 (s, 2H), 4.22 (t, J=5.8 Hz, 2H), 3.49–3.13 (m, 6H), 2.26 (m, 2H), 1.85–1.27 (m, 8H), 1.02 (m, 6H).

Theor. C$_{31}$H$_{39}$N$_3$O$_2$.2HCl.3/2H$_2$O: C, 63.58; H, 7.57; N, 7.18. Found: C, 63.69; H, 7.52; N, 7.17.

When in the above procedure, p-hydroxypropiophenone is employed as the starting material, 2-(4-dibutylaminopropoxyphenyl)-3-methyl-8-benzyloxyimidazo[1,2-a]pyridine is obtained as the resultant product.

When in the procedure of Example 6, 4,6-dimethyl-2-aminopyridine is used in place of 3-benzyloxy-2-aminopyridine, 2-(4-dibutylaminopropoxyphenyl)-5,7-dimethylimidazo[1,2-a]pyridine is obtained as the resultant product.

EXAMPLE 7

2-(4-Dibutylaminopropoxyphenyl)-3,8-dimethylimidazo[1,2-a]pyridine p-Hydroxypropiophenone (50 g, 0.33 mmol) was reacted with 1-bromo-3-chloropropane and the resulting compound reacted with bromine as described in Example 1. The resulting compound was reacted with 3-methyl-2-aminopyridine (1.7 g, 16 mmol) and the product reacted with dibutylamine as described in Example 1 to produce 2.4 g (62% yield) of the title compound as the HCl salt, mp 202° C. to 204° C. IR(KBr): 3420, 2620, 1650, 1605 cm$^{-1}$. MS: 408 (M+). $^1$H NMR (CD$_3$OD): δ 8.58 (d, J=6.5 Hz, 1H), 7.85–7.71 (m, 3H), 7.48 (t, J=6.7 Hz, 1H), 7.22 (d, J=8.7 Hz, 2H), 4.26 (t, J=5.8 Hz, 2H), 3.52–3.16 (m, 6H), 2.75 (s, 3H), 2.73 (s, 3H), 2.33 (m, 2H), 1.87–1.36 (m, 8H), 1.02 (m, 6H).

Theor. C$_{26}$H$_{37}$N$_3$O.3HCl.H$_2$O: C, 58.37; H, 7.91; N, 7.85. Found: C, 58.20; H, 7.98; N, 7.67.

When in the above procedure, 4,6-dimethyl-2-aminopyridine is used in place of 3-methyl-2-aminopyridine, 2-(4-dibutylaminopropoxyphenyl)-3,5,7-trimethylimidazo[1,2-a]pyridine is obtained as the resultant product.

When in any of the above procedures, 1-bromo-2-chloroethane, 1-bromo-4-chlorobutane or 1-bromo-5-chloropentane is used in place of 1-bromo-3-chloropropane, the corresponding 2-(4-dibutylaminoethoxyphenyl)-substituted imidazo[1,2-a]pyridines, 2-(4-dibutylaminobutoxyphenyl)-substituted imidazo[1,2-a]pyridines or 2-(4-dibutylaminopentoxyphenyl)-substituted imidazo[1,2-a]pyridines are obtained.

When in any of the above procedures, dimethylamine, diethylamine, dipropylamine, dipentylamine or dihexylamine is used in place of dibutylamine, the corresponding 2-(4-dimethyl-, 2-(4-diethyl-, 2-(4-dipropyl-, 2-4(dipentyl- or 2-(4-dihexylaminopropoxyphenyl)-substituted imidazo[1,2-a]pyridine derivatives are obtained.

EXAMPLE 8

2-(4-Dibutylaminopropoxybenzoyl)-8-methylimidazo[1,2-a]pyridine

To a solution of a α-bromoketone (60 g, 0.20 mol) in dimethylformamide (120 ml) was slowly added an aqueous solution of sodium hydroxide (8.6 g, 0.20 mol, in 50 ml of $H_2O$). The mixture was stirred at room temperature for 30 minutes, diluted with diethyl ether (500 ml) and washed once with $H_2O$ (500 ml). The ether layer was dried over $MgSO_4$, filtered and concentrated to give α-hydroxy-(4-chloropropoxy)propiophenone (30.5 g, 65% yield) as a yellow oil. $^1H$ NMR (CDCl$_3$): δ 7.93 (d, J=8.9 Hz, 2H), 6.98 (d, J=8.9 Hz, 2H), 5.12 (m, 1H), 4.21 (t, J=5.9 Hz, 2H), 3.77 (t, J=6.2 Hz, 2H), 2.28 (m, 2H), 1.46 (d, J=6.9 Hz, 3H).

To a solution of α-hydroxy-(4-chloropropoxy)propiophenone (30.5 g, 0.13 mol) in methylene chloride (250 ml) was added pyridinium chlorochromate (41 g, 0.19 mol) portionwise. The mixture was stirred at room temperature for 24 hours, filtered through Celite and concentrated. The dark oil was taken up in diethyl ether (500 ml), filtered again through Celite then concentrated to give α-keto-(4-chloropropoxy)propiophenone (18.7 g, 62% yield) as an amber oil. $^1H$ NMR (CDCl$_3$): δ 8.03 (d, J=8.9 Hz, 2H), 6.96 (d, J=8.9 Hz, 2H), 4.21 (t, J=5.9 Hz, 2H), 3.76 (t, J=6.2 Hz, 2H), 2.51 (s, 3H), 2.27 (m, 2H).

To a solution of α-keto-(4-chloropropoxy)propiophenone (18.7 g, 77.9 mmol) in diethyl ether (300 ml) was added bromine (4 ml, 77.9 mmol) dropwise. The solution was stirred at room temperature for 24 hours then poured into an aqueous saturated sodium bicarbonate solution (500 ml). The organic layer was separated, washed once again with an aqueous sodium bicarbonate solution, dried over $MgSO_4$, filtered and concentrated to give β-bromo-α-keto-(4-chloropropoxy)propiophenone (24.4 g, 98%) as an amber oil. $^1H$ NMR (CDCl$_3$): δ 8.02 (d, J=7.9 Hz, 2H), 6.99 (d, J=8.9 Hz, 2H), 4.40 (s, 2H), 4.23 (t, J=7.5 Hz, 2H), 3.76 (t, J=7.5 Hz, 2H), 2.70 (m, 2H).

A solution of 3-methyl-2-aminopyridine (1.6 g, 14.7 mmol) and β-bromo-α-keto -(4-chloropropoxy)propiophenone (4.7 g, 14.7 mmol) in ethanol (50 ml) was stirred at reflux for 3 hours. The mixture was concentrated and the resulting semi-solid was recrystallized from methanol acetone to give 2-(4-chloropropoxybenzoyl)-8-methylimidazo[1,2-a]pyridine as an off-white solid (2.4 g, 41% yield). $^1H$ NMR (CDCl$_3$): δ 9.94 (s, 1H), 9.59 (d, J=7.4 Hz, 1H), 8.21 (d, J=8.8 Hz, 2H), 7.73 (m, 1H), 7.10 (d, J=8.8 Hz, 2H), 6.74 (t, J=6.9 Hz, 1H), 4.25 (t, J=5.7 Jz, 2H), 3.77 (t, J=6.2 Hz, 2H), 2.76 (s, 3H), 2.30 (m, 2H).

A mixture of 2-(4-chloropropoxybenzoyl)-8-methylimidazo[1,2-a]pyridine (2.4 g, 6.0 mmol) in dibutylamine (30 ml) was stirred at reflux for 8 hours. The excess dibutylamine was removed by distillation and the resulting oil was flash chromatographed (silica gel, acetone) to give the free base of the title compound (2.5 g, 100% yield) as a thick oil. The HCl salt was prepared by dropwise addition of concentrated hydrochloric acid to a solution of the title compound in methanol, concentrated and recrystallized from methanol-acetone, mp 159° C. to 161° C. IR(KBr): 3420, 1650 cm$^{-1}$. MS: 421 (M+). $^1H$ NMR (CD$_3$OD): δ 8.89 (s, 1H), 8.72 (d, J=6.6 Hz, 1H), 8.15 (d, J=8.9 Hz, 2H), 7.89 (d, J=7.3 Hz, 1H), 7.48 (t, J=6.9 Hz, 1H), 7.21 (d, J=8.9 Hz, 2H), 4.29 (t, J=7 Hz, 2H), 3.26 (m, 6H), 2.73 (s, 3H), 2.33 (m, 2H), 1.79–1.35 (m, 8H), 1.02 (m, 6H).

Theor. $C_{26}H_{35}N_3O_2 \cdot 3HCl \cdot H_2O$: C, 56.88; H, 7.34; N, 7.65. Found: C, 56.42; H, 7.00; N, 7.60.

EXAMPLE 9

2-(4-Dibutylaminopropoxybenzoyl)-5,7-dimethylimidazo[1,2-a]pyridine

The title compound was prepared in accordance with Example 8 by reacting 4,6-dimethyl-2-aminopyridine (0.88 g, 6.6 mmol) with β-bromo-α-keto-(4-chloropropoxy)propiophenone and then reacting the resulting product with dibutylamine to yield 1.3 g of the free base (100% yield) which was converted to the HCl salt, mp 106° C. to 108° C. IR(KBr): 3400, 1650 cm$^{-1}$. MS: 435(M+). $^1H$ NMR (CD$_3$OD): δ 8.68 (s, 1H), 8.17 (d, J=8.9 Hz, 2H), 7.63 (s, 1H), 7.32 (s, 1H), 7.21 (d, J=8.9 Hz, 2H), 4.30 (t, J=6.2 Hz, 2H), 3.25 (m, 6H), 2.87 (s, 3H), 2.62 (s, 3H), 2.36 (m, 2H), 1.85–1.35 (m, 8H), 1.02 (m, 6H).

Theor. $C_{27}H_{37}N_3O_2 \cdot 3HCl$: C, 59.50; H, 7.40; N, 7.71. Found: C, 60.02; H, 7.76; N, 7.85.

EXAMPLE 10

2-(4-Dibutylaminopropoxybenzoyl)-7-methylimidazo[1,2-a]pyridine 4-methyl-2-aminopyridine (1.4 g, 12.5 mmol) was reacted with β-bromo-α-keto-(4-chloropropoxy)propiophenone as described in Example 8. The resulting product was reacted with dibutylamine as described in Example 8 to produce 2.9 g (75% yield) of the free base of the title compound which was converted to the HCl salt, mp 210° C. to 212° C. IR(KBr): 3460, 2640, 1650 cm$^{-1}$. MS: 421 (M+). $^1H$ NMR (CD$_3$OD): δ 8.89 (s, 1H), 8.77 (d, J=7.5 Hz, 2H), 8.12 (d, J=8.9 Hz, 2H), 7.77 (s, 1H), 7.48 (d, J=7.5 Hz, 2H), 7.20 (d, J=8.9 Hz, 2H), 4.30 (t, J=5.7 Hz, 2H), 3.38–3.16 (m, 6H), 2.65 (s, 3H), 2.35 (m, 2H), 1.81–1.34 (m, 8H), 1.02 (m, 6H).

Theor. $C_{26}H_{35}N_3O_2 \cdot 3HCl$: C, 58.81; H, 7.21; N, 7.91. Found: C, 58.79; H, 7.00; N, 7.79.

EXAMPLE 11

2-(4-Dibutylaminopropoxybenzoyl)-8-benzyloxyimidazo[1,2-]pyridine

The title compound was prepared according to Example 8 by reacting 3-benzyloxy-2-aminopyridine (2.2 g, 11 mmol) with β-bromo-α-keto-(4-chloropropoxy)-propiophenone and then reacting the resulting product with dibutylamine to produce 1.4 g (52% yield) of the free base which was converted to the HCl salt, mp 171° C. to 174° C. IR(KBr): 3400, 2620, 1660 cm$^{-1}$. MS: 513 (M+). $^1H$ NMR (CD$_3$OD): δ 8.87 (s, 1H), 8.44 (d, J=7.0 Hz, 1H), 8.12 (d, J=7.0 Hz, 2H), 7.66–7.35 (m, 7H), 7.20(d, J=7 Hz, 2H), 5.51 (brs, 2H), 4.31 (t, J=5.0 Hz, 2H), 3.41–3.14 (m, 6H), 2.32 (m, 2H), 1.65–1.34 (m, 8H), 1.02 (m, 6H).

Theor. $C_{32}H_{39}N_3O_3 \cdot 2HCl \cdot \frac{1}{2}H_2O$: C, 64.53; H, 7.11; N, 7.06. Found: C, 64.13; H, 7.22; N, 7.00.

EXAMPLE 12

2-(4-Dibutylaminopropoxybenzyl)-6-bromoimidazo[1,2-a]pyridine 5-bromo-2-aminopyridine (2.7 g, 15.7 mmol) was reacted with β-bromo-α-keto(4-chloropropoxy)propiophenone as described in Example 8. The resulting product was reacted with dibutylamine as described in Example 8 to produce 4.5 g (60% yield) of the free base of the title compound which was converted to the HCl salt, mp 214° C. to 216° C. IR(KBr): 3420, 2600, 2440, 1650 cm$^{-1}$. MS: 442 (M+). $^1$H NMR (CD$_3$OD ): δ 9.20 (s, 1H), 8.86 (s, 1H), 8.21 (d, J=8.7 Hz, 2H), 8.07–7.80 (m, 2H), 7.17 (d, J=8.7 Hz, 2H), 4.25 (m, 2H), 178–1.25 (m, 8H), 0.95 (m, 6H).

Theor. C$_{25}$H$_{32}$BrN$_3$O$_2$.2HCl: C, 53.68; H, 6.13; N, 7.51. Found: C, 53.28; H, 6.30; N, 7.52.

When in the above procedure, 2-aminopyridine or 3-hydroxy-2-aminopyridine is used in place of 5-bromo-2-aminopyridine, 2-(4-dibutylaminopropoxybenzoyl)imidazo[1,2-a]pyridine or 2-(4-dibutylaminopropoxybenzoyl)-8-hydroxyimidazo[1,2-a]pyridine is obtained.

When in any of the above procedures of Examples 8, 9, 10, 11 or 12, dimethylamine, diethylamine, dipropylamine, dipentylamine or dihexylamine is used in place of dibutylamine, the corresponding 2-(4-dimethyl, 2-(4-diethyl, 2-(4-dipropyl-, 2-(4-dipentyl, or 2-(4-dihexylaminopropoxybenzoyl)-substituted imidazo[1,2-a]pyridine derivatives are obtained.

EXAMPLE 13

3-(4-Dibutylaminopropoxybenzoyl)-8-methylimidazo[1,2-a]pyridine

To a solution of 3-methyl-2-aminopyridine (5.0 g, 46 mmol) in toluene (60 ml) was added dimethylformamide dimethylacetal (7.9 g, 6.2 mmol) dropwise and stirred at reflux for 6 hours. The mixture was concentrated to give 3-methyl-2-dimethylaminoamidinopyridine as an oil (7.0 g, 94% yield). $^1$H NMR (CDCl$_3$): δ 8.33 (s, 1H), 8.12–8.05 (m, 1H), 7.42–7.33 (m, 1H), 6.79 (d, d J=4.9 Hz, 1H), 3.08 (s, 6H), 2.30 (s, 3H).

A mixture of 3-methyl-2-dimethylaminoamidinopyridine (2.8 g, 17 mmol) and α-bromo-p-hydroxyacetophenone (3.6 g, 17 mmol) in ethanol (10 ml) was stirred at reflux for 2 hours. The mixture was cooled to room temperature and the resulting precipitate was collected by filtration and washed with cold ethanol to give 3-(4-hydroxybenzoyl)-8-methylimidazo[1,2-a]pyridine (2.6 g, 63% yield). $^1$H NMR (DMSO): δ 9.68 (d, J=8 Hz, 1H), 8.74 (s, 1H), 8.00–7.61 (m, 4H), 7.21 (d, J=7.2 Hz, 2H), 2.74 (s, 3H).

A mixture of 3-(4-hydroxybenzoyl)-8-methylimidazo[1,2-a]pyridine (2.3 g, 9.6 mmol), dibutylaminopropyl chloride (6.8 g, 33 mmol) and potassium hydroxide (1.3 g, 23 mmol) in methanol (60 ml) was stirred at reflux for 96 hours. The mixture was concentrated and the resulting oil was flash chromatographed (silica gel, 2.5% methanol in diethyl ether) to give 1.3 g (31% yield) of the free base of the title compound. The HCl salt was prepared by dropwise addition of concentrated hydrochloric acid to a solution of the free base in methanol, concentrated and recrystallized from acetone-ether to give the HCl salt of the title compound as an off-white solid, mp 105° C. to 107° C. IR(KBr): 3440, 2640, 1645, 1605 cm$^{-1}$. MS: 421 (M+). $^1$H NMR (CD$_3$OD): δ 9.66 (d, J=8 Hz, 1H), 8.74 (s, 1H), 8.00–7.61 (m, 4H), 7.20 (d, J=7.2 Hz, 2H), 4.29 (t, J=5 Hz, 2H), 3.41–3.15 (m, 6H), 2.75 (s, 3H), 2.31 (m, 2H), 1.80–1.42 (m, 8H), 1.02 (m, 6H).

Theor. C$_{26}$H$_{35}$N$_3$O$_3$.3HCl: C, 58.81; H, 7.21; N, 7.91. Found: C, 58.77; H, 7.17; N, 7.98.

EXAMPLE 14

3-(4-Dibutylaminopropoxybenzoyl)-6-bromoimidazo[1,2-a]pyridine

The title compound was prepared according to Example 13 by utilizing 5-bromo-2-aminopyridine (5.0 g, 28.9 mmol) in place of the 3-methyl-2-aminopyridine to produce 1.1 g (8.8% yield) of the free base which was converted to the HCl salt, mp 162° C. to 165° C. IR(KBr): 3430, 2650, 1650, 1610 cm$^{-1}$. MS: 442 (M—C$_3$H$_7$+). $^1$H NMR (CD$_3$OD); δ9.92 (m, 1H), 8.66 (s, 1H), 8.23 (d, d, J=9.95, 1.8 Hz, 1H), 8.06–7.95 (m, 3H), 7.18 (d, J=8.9 Hz, 2H), 4.28 (t, J=5.5 Hz, 2H), 3.39–3.14 (m, 6H), 2.32 (m, 2H), 1.80–1.34 (m, 8H), 1.02 (m, 6H).

For C$_{25}$H$_{32}$BrN$_3$O$_2$.3HCl.2H$_2$O: Theor.: C, 47.52; H, 6.22; N, 6.65; Cl, 17.85. Found: C, 47.60; H, 5.68; N, 6.66; Cl, 17.94.

When in the above procedure, 2-aminopyridine, 4-methyl-2-aminopyridine, 3-benzoyloxy-2-aminopyridine, 4,6-dimethyl-2-aminopyridine, or 3-hydroxy-2-aminopyridine is used in the starting material, the corresponding 3-(4-dibutylaminopropoxybenzoyl)imidazo[1,2-a]pyridine, 3-(4-dibutylaminopropoxybenzoyl)-7-methylimidazo[1,2-a]pyridine, 3-(4-dibutylaminopropoxybenzoyl)-8-benzyloxyimidazo[1,2-a]pyridine, 3-(4-dibutylaminopropoxybenzoyl)-5,7-dimethylimidazo[1,2-a]pyridine, or 3-(4-dibutylaminopropoxybenzoyl)-8-hydroxyimidazo[1,2-a]pyridine is obtained.

When in any of the above procedures of Examples 13 and 14, dibutylaminoethyl chloride, dimethylaminopentyl chloride, diethylaminobutyl chloride or dipentylaminopropyl chloride is employed as the alkylating agent, the corresponding 3-(4-dibutylaminoethoxy-, 3-(4-dimethylaminopentoxy-, 3-(4-diethylaminobutoxy)-, or 3-(4-dipentylaminopropoxybenzoyl)-substituted imidazo[1,2-a]pyridines are obtained.

EXAMPLE 15

Local Anesthetic Activity

The local anesthetic activity of the above compounds was tested as follows.

The test compounds were dissolved or suspended in a 0.5% aqueous methylcellulose solution containing 0.4% (v/v) of Tween 80, The polyoxyethylene derivative of a sorbitan ester. Doses of up to 100 mg/kg were administered orally by gagvage tube to groups of three male albino overnight-fasted mice (18 to 24 g) which were observed intermittently for one hour. The mice were gently restrained and 0.05 ml of a 1% (w/v) solution or suspension of the test compound was injected into the quadriceps femoris muscle of one hind leg. Five minutes later, the mice were individually placed on a wire mesh screen. The wire mesh screen was then inverted. Compounds that possess local anesthetic activity impaired the ability of the mice to grasp the inverted screen with the injected leg. The response to the test compounds was compared to a similarly treated vehicle control group of mice.

TABLE I

Local Anesthetic Effects of Representative
2- or 3-Aryl Substituted Imidazo[1,2-a]-
pyridines in Overnight-fasted Mice

| Compound (Example) | Concentration (in %) of Compound Causing Local Anesthetic Activity |
|---|---|
| 1 | 0.1 |
| 2 | 0.001 |
| 3 | 1.0 |
| 4 | 0.1 |
| 5 | 1.0 |
| 6 | 0.1 |
| 7 | 0.1 |
| 8 | 1.0 |
| 9 | 1.0 |
| 10 | 1.0 |
| 11 | 0.1 |
| 12 | 1.0 |
| 13 | 0.1 |
| 14 | 0.1 |

EXAMPLE 16

Anti-Secretory Activity

The antisecretory activity of the above compounds was determined by measuring gastric acid secretion using pylorus ligation in a modification of the procedure of Shay et al., *Gastroenterology* 26, 906 (1954). Basically, male Charles River Sprague Dawley derived rats weighing 150-300 grams were deprived of food but not water for 18-24 hours prior to use. Water was withheld during the experiment, however. The rats were weighed, anesthesized with ether and the pylorus ligated according to the method of Shay et al., supra. Treatment or vehicle control was then administered intraduodenally (i.d.) or subcutaneously (s.c.). Rats were housed two/cage and sacrificed with $CO_2$ four hours after ligation. The stomachs were removed, rinsed, and contents emptied into a graduated centrifuge tube. The tubes were centrifuged, the volume of gastric juice recorded, and any samples obviously contamined by feces, food or blood were eliminated. A 1 ml aliquot of gastric juice was titrated with 0.1N NaOH to a pH of 7.0-7.4. The volume of gastric juice secreted, the acid concentration, and the product of the volume times the concentration, i.e., the total amount of acid secreted, were measured. The amount of the acid output by the test compounds compared to the control is shown in Table II.

TABLE II

Antisecretory Effects of Representative
2- or 3-Acryl Substituted Imidazol[1,2-a]pyridines

| Compound (Example) | Dose (mg/kg) | % Acid Secreted |
|---|---|---|
| 1 | 20 | −41 |
| 2 | 20 | −91 |
| 3 | 20 | −18 |
| 6 | 20 | −16 |
| 7 | 20 | −54 |
| 8 | 20 | −27 |
| 9 | 20 | −27 |
| 13 | 40 | −49 |
| 14 | 20 | −18 |

EXAMPLE 17

Calcium Channel Blocking Activity

The calcium channel blocking activity of the above compounds was determined by measuring (A) the inhibition of calcium dependent smooth muscle contraction and (B) inhibition of nitrendipine binding as follows.

(A) Trachea from dogs sacrificed by excess KCl injection were stored overnight at 4° C. in oxygenated Krebs-Henseleit buffer. Tracheal rings, one cartilage segment wide (5-10 mm) were cut starting from the bronchial end. After cutting the cartilage, the trachealis muscle tissue was suspended in oxygenated Krebs-Henseleit buffer at 37° C. in a 25 ml tissue bath. After a 60 minute equilibration period, the tissues were challenged with 10 μM carbachol. After five minutes, the tissues were rinsed and allowed to rest 50 minutes. The tissues were then challened with 50 mM KCl and, after 30 minutes, the contracts were quantitated. The tissues were then rinsed and re-equilibrated for 50 minutes. Test compounds were then added at 10 μM for 10 minutes, and the tissues were rechallenged with 40 mM KCl. After 30 minutes, the contraction was recorded and used to determine the % inhibition of control.

The percent inhibition of smooth muscle contraction was calculated from response data before and after drug treatment.

$$\% \text{ inhibition} = 100 - 100 \frac{\text{(peak response after drug treatment)}}{\text{peak response before drug treatment}}$$

The results are shown in Table III.

(B) The inhibition of nitrendipine binding was determined by following the procedures of Bolger et al., *Biochem. Biophys. Res. Comm.* 104, 1604 (1982) and Ehlert et al., *Life Sciences* 30, 2191 (1982). Basically, female New Zealand white rabbits (1-2 kg) were sacrificed by cervical dislocation, and the heart was immediately removed, cleaned and chopped into small pieces. The tissue was homogenized in 5× volume of 0.05M Hepes buffer, pH 7.4. The homogenate was centrifuged at 400×g for 10 minutes; the supernatant was recentrifuged at 42,000×g for 90 minutes. The resulting membrane pellet was resuspended (0.7 ml/g weight) in 0.05M Hepes, pH 7.4, and stored at −70° C. until used. Each tube of the binding assay contained $^3$H-nitrendipine (0.05-0.50 nM), buffer, membranes (0.10 ml), and test compound in a total volume of 1.0 ml. After 90 minutes at 4° C., the bound nitrendipine was separated from the unbound by filtration to Whatman GF/C fibers. After rinsing, the filters were dried and counted in a liquid scintillation counter.

Non-specific binding of $^3$H-nitrendipine (that amount bound in the presence of excess unlabelled nitrendipine) was subtracted from the total bound to obtain specifically bound radiolabeled nitrendipine. The amount of specifically bound nitrendipine in the presence of a test compound was compared to that amount bound in the absence of a compound. A percent displacement (or inhibition) was then obtained. The concentration of test compound to obtain 50% inhibition of nitrendipine binding is shown in Table III.

TABLE III

Calcium Channel Blocking Effects
of Representative 2- or 3-Aryl
Substituted Imidazol[1,2a]pyridines

| Compound (Example) | A: % Inhibition of Smooth Muscle Contraction | B: $IC_{50}$ (μM) |
|---|---|---|
| 1 | 54 | 2.7 |
| 2 | 61 | 0.6 |
| 3 | 32 | 2.5 |
| 4 | 46 | 6.0 |

TABLE III-continued

Calcium Channel Blocking Effects of Representative 2- or 3-Aryl Substituted Imidazo[1,2a]pyridines

| Compound (Example) | A: % Inhibition of Smooth Muscle Contraction | B: IC$_{50}$ ($\mu$M) |
| --- | --- | --- |
| 6 | 35 | >8 |
| 7 | 27 | 1.9 |
| 8 | 58 | 0.6 |
| 9 | 39 | 2.2 |
| 10 | 42 | 1.6 |
| 11 | 18 | 2.3 |
| 12 | 50 | 3.0 |
| 13 | 56 | 0.53 |
| 14 | 62 | 0.2 |

What is claimed is:

1. A method for inhibiting gastric acid secretion of a mammal which comprises administering to a mammal an effective amount of a compound of the formula

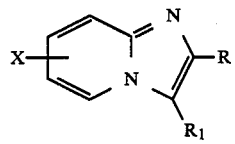 I where

X is one or more of hydrogen, halogen, hydroxy, alkoxy having 1-3 carbon atoms, benzyloxy, or $C_1$–$C_6$alkyl, combination;

R is H or Ar;

R$_1$ is H, CH$_3$ or Ar;

Ar is

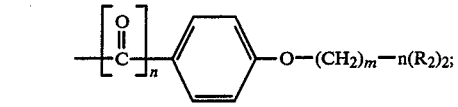

R$_2$ is $C_1$–$C_6$ alkyl;

N is 0 or 1 when R is Ar or 1 when R$_1$ is Ar; and m is 2-6, with the proviso that both R and R$_1$ are not Ar at the same time and at least one of R and R$_1$ is Ar, or a pharmaceutically acceptable salt thereof.

2. The method of claim 1 wherein the compound is selected from the group consisting of 2-(4-dibutylaminopropoxyphenyl)imidazo[1,2-a]pyridine; 2-(4-dibutylaminopropoxyphenyl)-8-methylimidazo[1,2-a]pyridine; 2-(4-dibutylaminopropoxyphenyl)-6-bromoimidazo[1,2-a]-pyridine; 2-(4-dibutylaminopropoxyphenyl)-7-methylimidazo[1,2-a]pyridine; 2-(4-butylaminopropoxyphenyl)-3,8-dimethylimidazo[1,2-a]pyridine; 2-(4-dibutylaminopropoxyphenyl)-8-hydroxyimidazo[1,2-a]pyridine; and 2-(4-dibutylaminopropoxyphenyl)-8-benzoyloxyimidazo[1,2-a]pyridine.

3. The method of claim 1 wherein the compound is selected from the group consisting of 2-(4-dibutylaminopropoxybenzoyl)-8-methylimidazo[1,2-a]pyridine; 2-(4-dibutylaminopropoxybenzoyl)-5,7-dimethylimidazo[1,2-a]pyridine; 2-(4-dibutylaminopropoxybenzoyl)-7-methylimidazo[1,2-a]pyridine; 2-(4-dibutylaminopropoxybenzoyl)-8-benzoyloxyimidao[1,2-a]pyridine; and 2-(4-dibutylaminopropoxybenzoyl)-6-bromoimidazo[1,2-a]pyridine.

4. The method of claim 1 wherein the compound is selected from the group consisting of 3-(4-dibutylaminopropoxybenzoyl)-8-methylimidazo[1,2-a]pyridine and 3-(4-dibutylaminopropoxybenzoyl)-6-bromoimidazo[1,2-a]pyridine.

* * * * *